(12) United States Patent
Takagaki et al.

(10) Patent No.: US 8,084,061 B2
(45) Date of Patent: Dec. 27, 2011

(54) BODY FAT-REDUCING AGENT

(75) Inventors: Kinya Takagaki, Fukuoka (JP); Masahito Tsubata, Fukuoka (JP)

(73) Assignee: Toyo Shinyaku Co., Ltd, Fukuoka-shi (JP)

( * ) Notice: Subject to any disclaimer, the term of this patent is extended or adjusted under 35 U.S.C. 154(b) by 0 days.

(21) Appl. No.: 12/579,725

(22) Filed: Oct. 15, 2009

(65) Prior Publication Data

US 2010/0028473 A1    Feb. 4, 2010

Related U.S. Application Data

(63) Continuation of application No. 11/572,558, filed as application No. PCT/JP2004/014906 on Oct. 1, 2004, now abandoned.

(30) Foreign Application Priority Data

Jul. 26, 2004    (JP) ................................. 2004-216923

(51) Int. Cl.
*A01N 65/00*    (2009.01)
(52) U.S. Cl. ...................................................... 424/725
(58) Field of Classification Search .................... None
See application file for complete search history.

(56) References Cited

U.S. PATENT DOCUMENTS

| | | | | |
|---|---|---|---|---|
| 5,324,516 A | * | 6/1994 | Pek et al. | 424/727 |
| 2005/0002992 A1 | * | 1/2005 | McCleary et al. | 424/439 |
| 2005/0202105 A1 | * | 9/2005 | Pero | 424/729 |

FOREIGN PATENT DOCUMENTS

| CN | 1141172 A | 1/1997 |
|---|---|---|
| CN | 1137256 | 6/2001 |
| CN | 1298938 | 6/2001 |
| CN | 1444865 A | 10/2003 |
| CN | 1502252 | 6/2004 |
| JP | 64-68318 A | 3/1989 |
| JP | 01-226824 | 9/1989 |
| JP | 8-73369 A | 3/1996 |
| JP | 2000-007694 | 1/2000 |

OTHER PUBLICATIONS

International Search Report for PCT/JP2004/014906 dated Nov. 16, 2004.

* cited by examiner

*Primary Examiner* — Michael Meller
(74) *Attorney, Agent, or Firm* — Turocy & Watson, LLP

(57) ABSTRACT

Described are body fat-reducing agents containing a processed pueraria flower as an active component. The body fat-reducing agent has a superior body fat-reducing effect. Furthermore, the body fat-reducing agent may contain at least one of a lipid absorption suppressing component and a lipid metabolism promoting component. A food product, which contains the body fat-reducing agent, provided according to the present invention has superior effects of preventing body fat accumulation and reducing body fat.

17 Claims, No Drawings

BODY FAT-REDUCING AGENT

CROSS-REFERENCE TO RELATED APPLICATIONS

This application is a Continuation of co-pending application Ser. No. 11/572,558 filed on Jan. 23, 2007, which is a National Phase application of PCT/JP2004/014906 filed on Oct. 1, 2004, which is claims the benefit of priority from Japanese Patent Application No. 2004-216923 filed Jul. 26, 2004, all of which are incorporated herein by reference.

TECHNICAL FIELD

The present invention relates to a body fat-reducing agent.

BACKGROUND ART

Kudzu, which is a leguminous plant, has been used as a raw material for food, a raw material of Chinese herbal medicines and the like for a long time. For example, the starch from kudzu has been used as a raw material of traditional Japanese confectionery. The root and flower of kudzu, which are respectively called pueraria root and pueraria flower, have been used as raw materials of Chinese herbal medicines for antipyretic, analgesic and spasmolytic effects, and improvement of symptoms such as sweating.

Among these, pueraria flower is known to contain various components, including flavonoids. In recent years, it has become clear that pueraria flower has an effect of improving hepatopathy, an effect of preventing a hangover, an effect of improving urinary nitrogen metabolism, and other effects, which are not provided by other leguminous plants (e.g., Japanese Patent No. 3454718, Japanese Patent Publication No. 08-032632, and Japanese Laid-Open Patent Publication No. 64-68318). However, pueraria flower do not appear to have been studied for its functions extensively, and a new use of pueraria flower is desired.

DISCLOSURE OF INVENTION

It is an object of the present invention to search a novel function of pueraria flower and develop new use of pueraria flower.

The inventors of the present invention conducted in-depth research on the functionality of pueraria flower and found that a processed pueraria flower, in particular, pueraria flower powder or pueraria flower extract, has a superior body fat-reducing effect, and thus, the present invention was achieved.

The present invention provides a body fat-reducing agent comprising a processed pueraria flower as an active component.

In a preferred embodiment, the body fat-reducing agent of the present invention further comprises at least one of a lipid absorption suppressing component and a lipid metabolism promoting component in addition to the processed pueraria flower.

The present invention also provides a food product comprising the above-described body fat-reducing agent.

BEST MODE FOR CARRYING OUT THE INVENTION

A body fat-reducing agent provided according to the present invention contains a processed pueraria flower as an active component. Preferably, the body fat-reducing agent further contains at least one of a lipid absorption suppressing component and a lipid metabolism promoting component in addition to the processed pueraria flower.

(Processed Pueraria Flower)

There is no particular limitation on the processed pueraria flower used in the present invention, as long as it is obtained by processing any flowers of pueraria plant, which belongs to the family Leguminosae. The pueraria flower includes flowers collected at various stages from flower bud to fully opened flower. It is preferable to use buds. A "processed pueraria flower" herein refers to a product obtained by subjecting the pueraria flower to at least one of drying, pulverization, and extraction treatments. Therefore, the processed pueraria flower includes dried pueraria flower, crushed pueraria flower, dried pulverized pueraria flower (i.e., pueraria flower powder), and pueraria flower extract. The pueraria flower extract includes extracts obtained by extraction from raw pueraria flower, crushed pueraria flower, dried pueraria flower, or pueraria flower powder. The forms of the pueraria flower extract may be liquid, paste, and powder, but are not limited to them.

The processed pueraria flower used in the present invention contains flavonoids such as isoflavones, saponin, tryptophan glycoside and the like and can preferably contain isoflavones and saponin. There is no particular limitation on the contents of these components. Preferably, isoflavones are contained at 3 wt % or more, more preferably 5 wt % to 90 wt % in terms of dry weight in the processed pueraria flower. Saponin is contained at preferably 1 wt % or more, more preferably 2 wt % to 50 wt %. The pueraria flower extract, which is a processed pueraria flower containing isoflavones and saponin abundantly, is preferably used. The pueraria flower extract has effects of preventing accumulation of visceral fat and subcutaneous fat and reducing these fats, and therefore preventing body fat accumulation and reducing body fat. Accordingly, it has an anti-obesity effect of decreasing body weight. Also, it has an effect of relieving lipid level in blood. The effect of preventing body fat accumulation, the effect of reducing body fat, the anti-obesity effect, and the effect of relieving lipid level in blood are, for example, better than those of a soybean extract, which contains isoflavones or saponin, in an equivalent amount, as shown in examples described later.

Hereinafter, methods for preparing the dried pueraria flower, pueraria flower powder, and pueraria flower extract, which are the above-described processed pueraria flower, will be described.

The dried pueraria flower is obtained by drying raw pueraria flower, preferably in the bud stage, by any methods such as drying in the sun and hot air drying. Preferably, such a drying is performed until the moisture content becomes 10 wt % or less.

The pueraria flower powder can be obtained by pulverizing the above-described dried pueraria flower. Pulverization is performed by any methods commonly used by those skilled in the art, for example, by using a ball mill, a hammer mill, a roller mill or the like.

The pueraria flower powder can also be obtained by crushing the collected raw pueraria flower using a masscolloider, a slicer, a comitrol or the like to give a crushed pueraria flower and drying the crushed pueraria flower.

The pueraria flower extract can be obtained by, for example, adding a solvent to collected raw pueraria flower, crushed pueraria flower, dried pueraria flower, or pueraria flower powder (hereinafter they are sometimes collectively referred to simply as a raw material for extraction) and optionally heating them to give an extract, and collecting the extract by centrifugation or filtration.

Examples of the solvent used in the above-described extraction include water, an organic solvent, and an aqueous organic solvent. Examples of the organic solvent include methanol, ethanol, n-propanol, n-butanol, acetone, hexane, cyclohexane, propylene glycol, methyl ethyl ketone, glycerin, methyl acetate, ethyl acetate, diethyl ether, dichloromethane, edible oils and fats, 1,1,1,2-tetrafluoroethane, and 1,1,2-trichloroethene. A polar organic solvent is preferable, ethanol, n-butanol, methanol, acetone, propylene glycol, and ethyl acetate are more preferable, and ethanol is most preferable.

There is no particular limitation on the extraction temperature, as long as the extraction temperature is not more than the boiling point of the solvent to be used. Although the extraction temperature varies depending on the solvent to be used, it is generally 4° C. to 130° C. in view of the degradation of an active component, for example. Preferably, the extraction temperature is 50° C. to 130° C., more preferably 70° C. to 100° C. When heating is performed for extraction, for example, heat extraction such as heating under reflux and supercritical fluid extraction can be employed. When heating is performed, heating may be performed under pressure.

The extraction time can be any length of time, for which a soluble component is extracted from the raw material for extraction in a sufficient amount, and the extraction time can be established as appropriate according to the extraction temperature and the like. Preferably, the extraction time is 30 minutes to 48 hours. For example, the extraction time may be 6 hours to 48 hours at a temperature below 50° C. The extraction time may be performed for 30 minutes to 24 hours at a temperature of 50° C. or above.

The pueraria flower extract can be optionally concentrated by any methods used by those skilled in the art, such as concentration under reduced pressure and freeze-drying, to give a liquid, paste or powder form of the extract. It should be noted that powdered pueraria flower extract is sometimes referred to as an extract powder.

Alternatively, the pueraria flower extract can be purified using a synthetic adsorbent (DIAION HP20, SEPABEADS SP825, Amberlite XAD4, MCIgelCHP20P, etc.) or a dextran resin (Sephadex LH-20, etc.), to enhance the concentrations of flavonoid, saponin and the like.

(Lipid Absorption Suppressing Component or Lipid Metabolism Promoting Component)

The body fat-reducing agent of the present invention preferably contains at least one of a lipid absorption suppressing component and a lipid metabolism promoting component in addition to the above-described processed pueraria flower. By combining the processed pueraria flower with the lipid absorption suppressing component or the lipid metabolism promoting component, a synergistic effect of suppressing lipid accumulation or reducing body fat can be obtained. Accordingly, an antidiabetic effect, an effect of preventing various symptoms caused by obesity, and other effects can be expected.

Examples of the lipid absorption suppressing component include a component that helps eliminate bile acids from the body, such as chitosan and derivatives thereof, psyllium, and proanthocyanidins; and a component providing a lipase inhibitory action, such as gallotannin and plants including loquat leaves and extracts of such plants. It is also possible to use plant extracts containing them abundantly, for example, a pine bark extract containing proanthocyanidins in a large amount. Proanthocyanidins and a plant extract (pine bark extract) containing proanthocyanidins are preferable.

Examples of the lipid metabolism promoting component include riboflavin and derivatives thereof, catechins, isomerized linoleic acid, caffeine, capsaicin, carnitine, coenzyme Q10 (CoQ10), α-lipoic acid, soybean peptide, amino acids, branched-chain amino acids (valine, isoleucine, leucine, etc.), arginine, phosphatidylcholine, allyl sulfide compounds, forskolin, bergenin, quercetin, astilbin, hydroxycitric acid, and salts of these. It is also possible to use plant extracts containing them, for example, extracts of tea, *Coleus forskohlii, Astilbe thunbergii, Engelhardtia chrysolepis*, soybean, red pepper, buckwheat, garlic, onion, coffee bean and the like. Coenzyme Q10 (CoQ10) is preferable.

Any lipid absorption suppressing components and lipid metabolism promoting components as listed above may be contained either alone or in combination according to the intended purpose. When in combination, for example, it is possible to contain two or more of lipid absorption suppressing components in combination or contain two or more of lipid metabolism promoting components in combination, or it is possible to combine one or more of lipid absorption suppressing components with one or more of lipid metabolism promoting components.

(Body Fat-Reducing Agent and Food Product Containing Body Fat-Reducing Agent)

A body fat-reducing agent and a food product, which contains the body fat-reducing agent, provided according to the present invention contain the above-described processed pueraria flower, and preferably contain at least one of the lipid absorption suppressing component and the lipid metabolism promoting component in addition to the processed pueraria flower. The body fat-reducing agent and the food product containing body fat-reducing agent of the present invention may contain other components, if necessary.

There is no particular limitation on the content of the processed pueraria flower in the body fat-reducing agent and in the food product containing body fat-reducing agent, and the content of the processed pueraria flower can be adjusted as appropriate according to the form of the processed pueraria flower or the dosage form of the body fat-reducing agent. Preferably, the content of the processed pueraria flower is 0.0001 wt % to 80 wt %, more preferably 0.001 wt % to 50 wt %. For example, when the pueraria flower powder is used to prepare the food product containing body fat-reducing agent, the pueraria flower powder may be added in an amount of 0.01 parts by weight or more, preferably 0.1 parts by weight or more with respect to 100 parts by weight of a food product. The upper limit of the amount of the pueraria flower powder to be added may be preferably 80 parts by weight, more preferably 50 parts by weight with respect to 100 parts by weight of a food product. When the pueraria flower extract is used to prepare the food product containing body fat-reducing agent, the pueraria flower extract may be added in an amount of 0.0001 parts by weight or more, preferably 0.001 parts by weight or more, more preferably 0.01 parts by weight or more in terms of dry weight with respect to 100 parts by weight of a food product. The upper limit of the amount of the pueraria flower extract to be added may be preferably 50 parts by weight, more preferably 30 parts by weight in terms of dry weight with respect to 100 parts by weight of a food product.

The content of the processed pueraria flower in the body fat-reducing agent or in the food product containing body fat-reducing agent can be determined based on the daily intake amount for an adult that depends on the types of the processed pueraria flower. Specifically, when the pueraria flower powder is used, the pueraria flower powder may be contained in such an amount that the daily intake amount for an adult is 0.1 g or more in terms of dry weight. The pueraria flower powder may be contained in such an amount that the upper limit of this intake amount is preferably 30 g, more preferably 10 g.

When the pueraria flower extract is used, the pueraria flower extract may be contained in such an amount that the daily intake amount thereof for an adult is 0.01 g or more in terms of dry weight. The pueraria flower extract may be contained in such an amount that the upper limit of this intake amount is preferably 3 g, more preferably 1 g.

The body fat-reducing agent and the food product containing body fat-reducing agent preferably contain at least one component of the lipid absorption suppressing component and the lipid metabolism promoting component, in addition to the processed pueraria flower. There is no particular limitation on the content of the lipid absorption suppressing component or the lipid metabolism promoting component (or a raw material containing the lipid absorption suppressing component or the lipid metabolism promoting component). Preferably, the content is 0.0001 wt % to 95 wt %, more preferably 0.0001 wt % to 70 wt %, even more preferably 0.01 wt % to 50 wt % in the body fat-reducing agent and the food product containing body fat-reducing agent. For example, peptides such as amino acids, branched-chain amino acids (valine, isoleucine, leucine, etc.), and soybean peptide; oils and fats such as isomerized linoleic acid; dietary fibers such as chitosan and derivatives thereof and psyllium and the like are contained preferably in an amount of 0.01 wt % to 95 wt %, more preferably 0.1 wt % to 90 wt % in the body fat-reducing agent and the food product containing body fat-reducing agent.

The body fat-reducing agent or the food product containing body fat-reducing agent may contain other components such as excipient, extender, binder, thickener, emulsifier, coloring agent, flavor, other food ingredients, seasoning, and pharmaceutical ingredients, if necessary. Examples of the food ingredients include royal jelly, propolis, vitamins (A, B, C, D, E, K, folic acid, pantothenic acid, biotin, derivatives of these, etc.), minerals (iron, magnesium, calcium, zinc, etc.), selenium, chitin and chitosan, lecithin, polyphenols (flavonoid and derivatives thereof, etc.), carotenoids (lycopene, astaxanthin, zeaxanthin, lutein, etc.), xanthine derivatives (caffeine, etc.), fatty acids, proteins (collagen, elastin, etc.), mucopolysaccharides (hyaluronic acid, chondroitin, dermatan, heparan, heparin, keratan, salts of these, etc.), amino sugars (glucosamine, acetylglucosamine, galactosamine, acetylgalactosamine, neuraminic acid, acetylneuraminic acid, hexosamine, salts of these, etc.), oligosaccharides (isomaltooligosaccharide, cyclic oligosaccharide, etc.), sphingolipid and derivatives thereof (phosphatidylcholine, sphingomyelin, ceramide, etc.), sulfur-containing compounds (alliin, cepaene, taurine, glutathione, methylsulfonylmethane, etc.), sugar alcohols, lignans (sesamin, etc.), animal or plant extracts containing them, root crops (turmeric, ginger, etc.), green leaves of grass family plants such as young barley leaf powder, and green leaves of cruciferous plants such as kale. As for the seasoning, sugar solutions, sugar alcohol solutions and the like can be used to control sweetness, for example.

There is also no particular limitation on the form of the body fat-reducing agent or the food product containing body fat-reducing agent. When the body fat-reducing agent or the food product containing body fat-reducing agent is in a liquid form, it can be used as a beverage. Moreover, it can be shaped into capsules such as hard capsules and soft capsules, tablets, or pills, optionally. Furthermore, it also can be prepared into the form of powder, granule, tea, tea bag, or candy, for example. Depending on the shape or the form of the body fat-reducing agent or the food product containing body fat-reducing agent, the body fat-reducing agent or the food product containing body fat-reducing agent may be eaten as it is, or may be dissolved in water, hot water, bovine milk or the like and then drunk according to individual preference. Moreover, when the body fat-reducing agent or the food product containing body fat-reducing agent is pulverized and prepared in the form of tea bag or the like, it is also possible to disperse or dissolve the components thereof in a liquid for drinking. Furthermore, for example, the body fat-reducing agent or the food product containing body fat-reducing agent may also be used in fermented plant juice, vegetable juice (e.g., carrot juice), plant extracts, fruit juice and the like. Since the body fat-reducing agent or the food product containing body fat-reducing agent contains pueraria flower, not only the palatability can be improved, but also a functional or nutritious beverage can be provided.

The body fat-reducing agent and the food product containing body fat-reducing agent, which contain the processed pueraria flower as an active component, have a superior effect of reducing body fat. The effect is better than that of an extract from soybean which belongs to the family Leguminosae as kudzu. Therefore, by virtue of the newly found function, that is, an effect of reducing body fat, of the processed pueraria flower, the processed pueraria flower can be utilized as a body fat-reducing agent or a food product for preventing body fat accumulation and reducing body fat. The body fat-reducing agent or the food product containing body fat-reducing agent further can contain the lipid absorption suppressing component or the lipid metabolism promoting component in addition to the processed pueraria flower, and thus, a synergistic effect of reducing body fat can be expected by these components and the processed pueraria flower. In other words, a combination of the processed pueraria flower with the lipid absorption suppressing component or the lipid metabolism promoting component can be expected to have a better effect of reducing body fat than a mere combination at least two of a component for suppressing sugar absorption, a component for suppressing lipid absorption, a component for promoting sugar metabolism, and a component for promoting lipid metabolism.

EXAMPLES

Hereinafter, the present invention will be described by means of examples. However, it should be appreciated that the description of these examples is not intended to limit the scope of present invention, and various modifications can be made within the scope of the invention as defined in the appended claims.

Example 1

Verification of the Body Fat-Reducing Effect

The body fat-reducing effect was verified in the following manner. First, 21 male SD rats (CHARLES RIVER LABORATORIES JAPAN, INC.) at the age of 4 weeks were given a standard feed (MF feed, produced by Oriental Yeast Co., Ltd.) for acclimation for one week. Then, the rats were divided into 3 groups so that the average body weight was almost equal among the groups.

Separately, a feed was prepared by adding cholesterol, sodium cholate, corn oil, a hot water extract of dried powder of pueraria flower (containing 10 wt % of isoflavones: produced by Ohta's Isan Co., Ltd.) to the standard feed so that these components are contained in the resultant feed in proportions of 1 wt %, 0.25 wt %, 10 wt %, and 5 wt %, respectively. This feed is referred to as a test feed.

A feed was prepared in the same manner as the above-described test feed, except that a soybean extract (containing 10 wt % of isoflavones: produced by FUJI OIL CO., LTD.) was added instead of the hot water extract of dried powder of pueraria flower so that this soybean extract is contained in the resultant feed in a proportion of 5 wt %. This feed is referred to as a comparative feed. Moreover, a feed was prepared in the same manner as the above-described test feed, except that the hot water extract of the dried powder of pueraria flower was not added. This feed is referred to as a control feed.

The rats in one group of the above-described three groups were allowed to freely ingest the test feed. Another group was allowed to freely ingest the comparative feed, and the other group was allowed to freely ingest the control feed.

On day 28 from the start of the ingestion, the rats were fasted for one day, and after fasting, the body weight of each rat was measured. Then, the rats were dissected, and perirenal adipose tissue was removed to measure the fat weight. After the measurement, the fat weight (%) per body weight was calculated using formula (I) below. Table 1 shows the results.

$$\text{Fat weight (\%) per body weight} = \frac{\{\text{Fat weight (g)}\}}{\{\text{Body weight (g)}\}} \times 100 \quad (I)$$

TABLE 1

|  | Test feed | Comparative feed | Control feed |
|---|---|---|---|
| Component | Pueraria flower extract | Soybean extract | — |
| Fat weight (%) per body weight | 1.15 ± 0.22 | 1.36 ± 0.17 | 1.51 ± 0.19 |

The values are shown as average values ± standard deviation.

According to Table 1, the fat weight per body weight in the group ingesting the feed (test feed), containing a pueraria flower extract, is lower than those in the groups ingesting the control feed and the comparative feed, containing a soybean extract. Therefore, it is found that the test feed has a better fat-reducing effect than the comparative feed and the control feed. Thus, it is found that a food product containing a processed pueraria flower (pueraria flower extract) has a superior body fat-reducing effect.

Example 2

Examination of the Body Fat-Reducing Effect and the Anti-Obesity Effect

An effect of the processed pueraria flower regarding fat accumulation in subcutaneous fat and visceral fat was examined in the following manner using female ICR mice at the age of 7 weeks. First, 35 ICR mice were given a standard feed (MF feed, produced by Oriental Yeast Co., Ltd.) for acclimation for one week. Then, the mice were divided into 5 groups of 7 each so that the average body weight per group was uniform.

Separately, a feed (test feed 1) was prepared by adding 5 wt % of pueraria flower extract (containing 10 wt % of isoflavones and 1 wt % of saponin, produced by Ohta's Isan Co., Ltd.), 40 wt % of beef tallow, and 9 wt % of granulated sugar to the standard feed.

A feed (test feed 2) was prepared in the same manner as the above-described preparation method of the test feed 1, except that 5 wt % of pine bark extract containing 75 wt % of proanthocyanidins and 5 wt % of catechins (this pine bark extract contained 40 wt % of oligomeric proanthocyanidins, product name: Flavangenol (registered trademark), produced by TOYO SHINYAKU Co., Ltd.) was further added to the standard feed in addition to the above-described pueraria flower extract.

A feed (test feed 3) was prepared in the same manner as the above-described preparation method of the test feed 1, except that 1 wt % of CoQ10 (NISSIN PHARMA INC.) was further added to the standard feed in addition to the above-described pueraria flower extract.

A feed (comparative feed) was prepared in the same manner as the above-described preparation method of the test feed 1, except that a soybean extract (containing 10 wt % of isoflavones, produced by FUJI OIL CO., LTD.) was used instead of the pueraria flower extract.

A feed (control feed) was prepared in the same manner as the above-described preparation method of the test feed 1, except that the pueraria flower extract was not added.

The mice in the above-described 5 groups were allowed to freely ingest the test feeds 1 to 3, the comparative feed, and the control feed, respectively.

On day 25 from the start of the free ingestion, the body weight of each mouse was measured. After the measurement, the body weight increasing rate (%) was calculated using formula (II) below. Table 2 shows the results.

$$\text{Body weight increasing rate (\%)} = \frac{\left(\left(\begin{array}{c}\text{Body weight on day 25}\\\text{after start of ingestion}\end{array}\right) - \left(\begin{array}{c}\text{Body weight}\\\text{before ingestion}\end{array}\right)\right)}{(\text{Body weight before ingestion})} \times 100 \quad (II)$$

Furthermore, subcutaneous fat of each mouse was measured by an X-ray CT for experimental animals (product name: LATheata, produced by ALOKA CO., LTD.). Then, blood was collected from fundus oculi of each mouse, and thereafter the mice were dissected, and retroperitoneal fat and parametrial fat were removed to measure the total weight of these fats (the weight of visceral fat). Table 2 also shows the results.

Furthermore, for the blood collected from the mice ingesting the test feed 1 or the control feed, the triglyceride concentration in blood was measured using a measuring kit (produced by Wako Pure Chemical Industries, Ltd.). Table 3 shows the results.

TABLE 2

|  | Component | Body weight increasing rate (%) | Visceral fat (g) | Subcutaneous fat (g) |
|---|---|---|---|---|
| Test feed 1 | Pueraria flower extract | 30.8 ± 1.9* | 1.21 ± 0.68* | 2.95 ± 1.38* |
| Test feed 2 | Pueraria flower extract Pine bark extract | 29.1 ± 1.7* | 1.11 ± 0.71* | 2.82 ± 1.48* |

TABLE 2-continued

| | Component | Body weight increasing rate (%) | Visceral fat (g) | Subcutaneous fat (g) |
|---|---|---|---|---|
| Test feed 3 | Pueraria flower extract CoQ10 | 28.7 ± 1.7* | 1.12 ± 0.58* | 2.91 ± 1.41* |
| Comparative feed | Soybean extract | 33.1 ± 1.5 | 1.40 ± 0.55 | 3.42 ± 2.16 |
| Control feed | — | 34.1 ± 2.4 | 2.34 ± 1.01 | 4.56 ± 1.62 |

*Significant difference versus the control feed, $p < 0.05$
The values are shown as average values ± standard deviation.

The results in Table 2 show that in the groups ingesting the test feeds 1 to 3, containing a pueraria flower extract, the body weight increasing rate was smaller and accumulation of both subcutaneous fat and visceral fat was more suppressed when compared with the groups ingesting the control feed, not containing a pueraria flower extract, or the comparative feed, containing a soybean extract. These findings indicate that a processed pueraria flower which is used in the present invention has a superior body fat-reducing effect and can be utilized as a body fat-reducing agent. Moreover, since the processed pueraria flower which is used in the present invention suppresses body weight increasing, it can also be utilized as an anti-obesity agent. The body weight increasing rate was smaller and also accumulation of subcutaneous fat and visceral fat was more suppressed particularly in the groups ingesting the test feed 2, containing a pueraria flower extract and a pine bark extract, or the test feed 3, containing a pueraria flower extract and CoQ10. These findings indicate that even superior body fat-reducing effect and anti-obesity effect tend to be obtained by combining pueraria flower with a pine bark extract (proanthocyanidins) or CoQ10.

TABLE 3

| | Component | Triglyceride concentration in blood (mg/dL) |
|---|---|---|
| Test feed 1 | Pueraria flower extract | 76.4 ± 21.9 |
| Control feed | — | 109.7 ± 62.0 |

The values are shown as average values ± standard deviation.

The results in Table 3 show that the blood triglyceride concentration in the group ingesting the test feed 1, containing a pueraria flower extract, was lower than in the case of the control feed, not containing a pueraria flower extract. This finding indicates that a processed pueraria flower which is used in the present invention also has a superior effect of relieving lipid level in blood and can also be utilized as an agent for relieving lipid level in blood.

Production Example 1

A food product (tablet) containing a pueraria flower extract and a lipid absorption suppressing component or lipid metabolism promoting component was produced according to the following formulation (mixing amount). The tablets produced weighed 200 mg per tablet. Numerical values in the formulation (mixing amount) shown below are expressed in wt %.

| <Mixed components in the tablets> | Mixing amount (wt %) |
|---|---|
| Pueraria flower extract (produced by Ohta's Isan Co., Ltd.) | 5 |
| Pine bark extract (produced by TOYO SHINYAKU Co., Ltd.) | 1 |
| Ascorbic acid | 10 |
| Crystalline cellulose | 14 |
| Sucrose ester | 4 |
| Maltitol | 35 |
| Silicon dioxide | 1 |
| Trehalose | 30 |

Production Example 2

A food product (granule) containing a pueraria flower powder and a lipid absorption suppressing component or lipid metabolism promoting component was produced according to the following formulation (mixing amounts). Numerical values in the formulation (mixing amounts) shown below are expressed in wt %.

| <Mixed components contained in the granules> | Mixing amount (wt %) |
|---|---|
| Pueraria flower dried powder | 25 |
| Soybean peptide | 25 |
| Tea catechin | 10 |
| Crystalline cellulose | 10 |
| Maltitol | 30 |

INDUSTRIAL APPLICABILITY

As described above, by ingestion of a processed pueraria flower as an active component, a superior body fat-reducing effect is provided, and furthermore, an anti-obesity effect and an effect of relieving lipid level in blood can also be obtained. In an embodiment, by ingestion of a processed pueraria flower in combination with a lipid absorption suppressing component or lipid metabolism promoting component, an even more superior body fat-reducing effect can be obtained. The body fat-reducing agent containing a processed pueraria flower as an active component according to the present invention is useful as a food product, a pharmaceutical product and the like.

The invention claimed is:
1. A method for reducing body fat, in an individual in need thereof consisting essentially of administering a body fat reducing agent which has a therapeutically effective amount of a pueraria flower extract and a therapeutically effective amount of a pine bark extract to an individual that needs to have their body fat reduced.

2. The method of claim 1, wherein the pueraria flower extract comprises 5 wt % to 90 wt % isoflavones.

3. The method of claim 1, wherein the pueraria flower extract comprises 2 wt % to 50 wt % saponin.

4. The method of claim 1, wherein the pueraria flower extract comprises isoflavones and saponin.

5. The method of claim 1, wherein the body fat-reducing agent comprises 0.0001 wt % to 80 wt % of the pueraria flower extract.

6. The method of claim 1, wherein the body fat-reducing agent comprises 0.001 wt % to 50 wt % of the pueraria flower extract.

7. The method of claim 1, wherein the individual ingests 0.1 g to 30 g per day of pueraria flower powder.

8. The method of claim 1, wherein the individual ingests 0.1 g to 10 g per day of pueraria flower powder.

9. The method of claim 1, wherein the individual ingests 0.01 g to 3 g per day of pueraria flower extract.

10. The method of claim 1, wherein the individual ingests 0.01 g to 1 g per day of pueraria flower extract.

11. The method of claim 1, wherein the body fat-reducing agent comprises 0.0001 wt % to 95 wt % of the pine bark extract.

12. The method of claim 1, wherein the body fat-reducing agent comprises 0.01 wt % to 50 wt % of the pine bark extract.

13. A method for reducing body fat, in an individual in need thereof consisting essentially of administering a body fat reducing agent which has a therapeutically effective amount of a pueraria flower extract and a therapeutically effective amount of a pine bark extract to an individual that needs to have their body fat reduced,
   wherein the body fat-reducing agent is ingested for at least 25 days.

14. The method of claim 13, wherein the individual ingests 0.1 g to 30 g per day of pueraria flower powder.

15. The method of claim 13, wherein the individual ingests 0.1 g to 10 g per day of pueraria flower powder.

16. The method of claim 13, wherein the individual ingests 0.01 g to 3 g per day of pueraria flower extract.

17. The method of claim 13, wherein the individual ingests 0.01 g to 1 g per day of pueraria flower extract.

* * * * *